United States Patent [19]

Cummings

[11] 4,308,128
[45] Dec. 29, 1981

[54] PRODUCING LIQUID HYDROCARBON STREAMS BY HYDROGENATION OF FOSSIL-BASED FEEDSTOCK

[75] Inventor: Donald R. Cummings, Cheltenham, England

[73] Assignee: D.U.T. Pty. Ltd., Sydney, Australia

[21] Appl. No.: 171,961

[22] Filed: Jul. 24, 1980

[51] Int. Cl.³ .......................... C10G 1/04; C10G 7/00
[52] U.S. Cl. ....................................... 208/86; 208/87; 208/92; 208/100
[58] Field of Search ....................... 208/92, 95, 58, 60, 208/86, 94, 100, 102, 104, 87

[56] References Cited

U.S. PATENT DOCUMENTS

| | | | |
|---|---|---|---|
| 3,224,958 | 12/1965 | Schlinger | 208/95 |
| 3,228,467 | 1/1966 | Schlinger | 208/58 |
| 3,537,977 | 11/1970 | Smith, Jr. | 208/92 |
| 3,905,892 | 9/1975 | Gregoli | 208/95 |

Primary Examiner—T. Tufariello
Attorney, Agent, or Firm—Fred A. Keire

[57] ABSTRACT

An economic route to transport fuels from low grade feedstocks containing organic polycyclic components and mineral and/or metallic components comprises separating the feedstock into (a) a residue containing fuel values and substantially all of the mineral and metallic components and (b) a liquid hydrocarbon fraction; hydrogenating the liquid hydrocarbon fraction; providing hydrogen for the hydrogenation by steam reforming methane-containing gas recovered from the hydrogenated material; and providing the heat for the steam reforming by immersing the reformer reactor tubes in a fluidized bed heated by combustion of residue from the separation step. If the fluidized bed is pressurized, the process can be made substantially self-contained with all the heat and power requirements for steam generation and feedstock compression for hydrogenation and steam reforming being recovered from the flue gas.

6 Claims, 3 Drawing Figures

PRODUCING LIQUID HYDROCARBON STREAMS BY HYDROGENATION OF FOSSIL-BASED FEEDSTOCK

This invention relates to the treatment of a fossil-based feedstock containing a substantial proportion of high molecular weight organic polycyclic components to recover a more valuable liquid hydrocarbon stream e.g. suitable for use as or in the production of transport fuels such as gasoline, diesel oil, gas oils, kerosine, aviation gasoline and aviation turbine fuel.

High molecular weight organic polycyclic components are found in substantial quantities in crude oils, in which context asphaltenes form a significant proportion of these polycyclic components, and are concentrated in the residues of such oils after distillation. They are also present in substantial amounts in solid fossil fuels such as coal, peat, lignite and shale, and also in tar sands.

Such polycyclic components are often heterocyclic and can include in their structures atoms of oxygen, sulphur and/or metals.

Examples of fossil-based feedstocks with which this invention is concerned are, thus, oil-based feedstocks such as crude oils, distillation residues of crude oils such as atmospheric residues and vacuum residues, vis-breaking residues, cracking residues and oils derived from the distillation of shale, and solid materials such as coal, lignite, peat, shale and tar sands.

It is known that valuable liquid hydrocarbon streams such as are suitable for use as or in the production of transport fuels may be derived from such fossil-based feedstocks by hydrogenation.

In one method, the hydrogen for the hydrogenation is generated by gasifying a portion of the fossil-based feedstock or a residue derived from it such as the char formed in the solvent extraction of a coal. However, the capital costs of gasification plants are so high that even with the benefit of using a cheap feedstock such as char for the hydrogen, the process has rarely been commercially employed.

In another method, such as described in BP Nos. 1289158 and 1525436, it is proposed to produce hydrogen for the hydrogenation by steam reforming a gaseous hydrocarbon stream which is formed as a byproduct of the hydrogenation. The capital costs of steam reforming can be less than half those of gasification but premium gaseous or high grade liquid fuels are required to heat the reformer. This is because with the known heater designs, the accurate control of reformer tube temperatures, which is essential for the avoidance of premature tube failure and/or carbon build-up on the catalyst, can only be achieved if such fuels are employed, and even then optimum reaction conditions cannot be ensured.

In practice this means that either a part of the gaseous hydrocarbon stream must be employed as the fuel or a separate source of supply of the fuel is required. In the former case, the balance of the gaseous hydrocarbon stream is insufficient to produce the required amount of hydrogen and in the latter case, the capital cost advantage of steam reforming over gasification stands to be offset largely or wholly by the higher cost of the fuel.

Whichever alternative is adopted, therefore, producing the hydrogen accounts for a large proportion of the overall cost of the process and can account for as much as 30% to 50% of the value of the liquid hydrocarbon product. For this reason, the industry has recognised for many years the importance of this step of the process and much effort has been directed at reducing the expense of it. For example, attention has been directed to improving the selective utilisation of the hydrogen to the production of the desired products, to reducing the capital cost of the gasification route, to improving heat recovery from the steam reforming step, and even to re-siting refinery operations. However, although the steam reforming route still has a major capital cost advantage over the known alternatives, no attention appears to have been directed to reducing costs by use of a low grade fuel to provide the heat for the reforming and no practicable proposal has been put forward.

According to the present invention there is provided a process which comprises the steps of separating a fossil-based feedstock containing a substantial proportion of high molecular weight organic polycyclic components and also mineral and/or metallic components to provide (a) a residue containing fuel values and substantially all of said mineral and/or metallic components and (b) a liquid hydrocarbon fraction; reducing the average molecular weight of said liquid hydrocarbon fraction by hydrogenation; fractionating hydrogenation material thereby obtained to form a gaseous fraction containing substantially all the methane in said material and at least one liquid hydrocarbon stream; and providing hydrogen for said hydrogenation by steam reforming a methane-containing gas provided from said gaseous fraction, the reforming being effected at elevated temperature in a reactor vessel which is at least partly immersed in a fluidised bed of finely divided solid material which is heated by combustion of a fuel provided at least in part, and preferably entirely or substantially entirely, from said residue of said separation step.

By means of the invention, the cost of providing the heat for the stream reforming step, which cost forms a very significant proportion of the cost of producing the hydrogen, is substantially reduced without very much change in the capital cost of the steam reforming equipment, thereby providing an important and substantial saving in the overall cost of the production of the liquid hydrocarbons.

Other advantages also accrue from the use of a fluidised bed combustor; in particular, improved temperature control through more uniform transfer of heat to the reformer tube walls, elimination of the need to ensure an exact distribution of feed to each reformer tube, higher heat transfer rates with consequent reduction in the temperature of the flue gas leaving the reformer tube zone, lower temperature differences between heat source and the tube wall, greater freedom in the shape and orientation of the reactor tubes, more compact arrangement of tubes and consequential reduction in overall apparatus size and refractory requirements, lower combustion flame temperature with consequential reduction in concentration of oxides of nitrogen in the flue gas, possibility of upward or downward flow of reaction mixture through the reactor tubes and, with the former, of using fluidised catalyst beds in the tubes, and superior turn down and flexibility of process control.

A particular advantage of the process of the invention, however, is that the fluidised bed may be under superatmospheric pressure and thus the pressure drop across the reformer reactor tube walls may be reduced or eliminated thereby permitting extended tube life, higher operating temperatures, use of thinner tube walls, use of lower grade tube material, higher pressures in the reformer tubes or a combination of two or more of these possibilities. It also provides the possibility of using ceramic tubes under compression, in which mode they offer better performance.

A further advantage of operating the fluidized bed combustor at superatmospheric pressure is that power for the process of the invention may be provided by expanding the flue gas from the combustor through an expansion engine such as a turbine. The extraction of energy from the flue gas in this manner is more efficient than the conventional raising of high pressure superheated steam and the subsequent use of the steam to drive compressors or electricity generators. Moreover, by suitable choice of the amount of excess oxidant gas supplied to the combustor and of the presssure of the combustor, all or substantially all the power requirements of the process, and in particular for compressing the oxidant gas for the fluidised bed combustor, and compressing gases and pumping liquids in the process, e.g. for the hydrogenation and steam reforming steps, may be satisfied in this manner.

Thus, the process may be substantially self-contained, with all the fuel requirements for the steam reformer being provided by the residue from the separation step, all the hydrogen for the hydrogenation being provided from the gaseous material produced by the hydrogenation and all the energy requirements being provided by expansion of the flue gas from the fluidised bed combustor.

The feedstock for the process may be a crude oil, a liquid residue derived from crude oil, an oil derived from tar sands, or a solid, which may be an oil residue or a solid fossil fuel such as coal or an oil-bearing shale or a tar sand. The nature of the separation step will be determined by the nature of the feedstock. The following Table indicates possible separation steps for various feedstocks which may be used in the process of this invention. However, it is to be understood that the feedstocks which are suitable for use in the process of this invention are not limited to those listed in the Table and the processes indicated as suitable for use for separating these feedstocks in accordance with the first step of the process of the invention do not cover all the possible processes. Other feedstocks and separation processes will not be apparent to those skilled in the art.

So far as concerns oil-based materials, the invention is particularly suited to the treatment of heavy crude oils, producable tar oils such as Orinoco Tar which has API gravities in the order of 8 to 12, and crude oil residues having API gravities in the same range. Coal, lignite and tar sands are also particularly suitable feedstocks.

TABLE

| Feedstock | Separation Step |
| --- | --- |
| crude oil<br>shale oil<br>oil from tar sands | (a) 1 or 2 or 1+3<br>(b) (1 or 2 or 1+3) + (4 or 5 or 6 or 7)<br>(c) (1 or 2 or 1+3) + (4 or 5) + (6 or 7) |
| residue of atmospheric distillation of crude oil | (a) 3 or 4 or 5 or 6 or 7<br>(b) 3 + (4 or 5 or 6 or 7)<br>(c) 3 + (4 or 5) + (6 or 7)<br>(d) (4 or 5) + (6 or 7) |
| residue of vacuum distillation of crude oil<br>vis-breaker residue<br>cracking residue | (a) 4 or 5 or 6 or 7<br>(b) (4 or 5) + (6 or 7)<br>6 or 7 |
| coal<br>lignite<br>peat | (a) solvent extraction (which term includes supercritical solvent extraction and solvent extraction with simultaneous hydrogenation e.g. by hydrogenating a coal-in-oil slurry with recycle of hydrogenated oils) |
| oil-bearing shale<br>tar sands | (b) carbonisation (including flash carbonisation)<br>distillation or solvent extraction<br>separation of oil or distillate by paraffinic solvent extraction or by coking or by distillation, to produce a fuel-containing sand residue and a liquid hydrocarbon fraction |

KEY
1. Atmospheric distillation
2. Vacuum distillation
3. Vacuum distillation of the residue from atmospheric distillation
4. Vis-breaking the residue of atmospheric or vacuum distillation
5. Thermal cracking the residue of atmospheric or vacuum distillation
6. Coking the residue of atmospheric or vacuum distillation or the residue or vis-breaking or of cracking
7. Deasphalting the residue of atmospheric or vacuum distillation or the residue of vis-breaking or of cracking The terms "atmospheric distillation" and "vacuum distillation" include both single- and multi-stage distillations.

The separation may also comprise hydrocracking oil with an ebullated bed operated in such fashion as to leave asphaltene substantially unreacted, e.g. as in the H-Oil process.

The immediate liquid product of the separation step may be subjected to further treatment, e.g. fractionation, to provide the liquid hydrocarbon fraction to be hydrogenated. For example, where the feedstock for the process is a solid substantially infusible fuel such as coal, lignite or peat and the separation step includes solvent extraction, it will generally be desirable to distil the liquid product to recover solvent for recycle.

In general, no further processing of the distillate from the step of separating oil-based feedstocks will be required but a further processing step is not excluded.

Thus, to summarise, the step of separating the feedstock into the residue and the liquid hydrocarbon fraction may comprise a single step, e.g. atmospheric or vacuum distillation, or a series of process steps with the residue and the liquid hydrocarbon fraction being the products of different steps of the operation; e.g. as in the distillation of crude oil followed by deasphalting the distillation residue, wherein the liquid hydrocarbon fraction may be provided from the distillation (optionally after further fractionation) and the residue may be provided from the deasphalter, or as in the solvent extraction of coal, peat or lignite, where the residue may be the solid residuum of the solvent extraction and the liquid hydrocarbon fraction is provided from the solution after treatment to recover the solvent.

All the processes employed singly or in combination to effect the separation in accordance with the invention may be conducted in accordance with well known principles. The nature of the residue and of the liquid hydrocarbon fraction can vary widely and will depend upon the nature of the feedstock and of the process or processes employed to effect the separation. For example, where the feedstock is crude oil or is derived from crude oil, the residue from atmospheric or vacuum distillation or from cracking or vis-breaking may be a more or less viscous liquid whereas the residue from coking or deasphalting will normally be a tarry or asphaltic solid or semi-solid at ambient temperatures. The residue from the carbonisation or solvent extraction of coal, lignite or peat will be a carbonaceous solid.

The liquid hydrocarbon fraction employed for the hydrogenation may vary widely in composition, viscosity and average molecular weight, depending on the nature of the feedstock and kind of process or processes employed for the separation. More than one liquid hydrocarbon fraction may be produced by the separation and one or more of the fractions may be hydrogenated. Where two or more fractions are to be hydrogenated, the hydrogenations may be effected in separate hydrogenation reactors. For example, where the separation includes distillation of oil employing atmospheric and vacuum distillations, fractions from both these distillations may be separately hydrogenated.

The second step of the process of the invention comprises hydrogenation of the liquid hydrocarbon fraction to reduce its average molecular weight. The hydrogenation may be conducted in known manner and employing well-established conditions. In general it involves contacting the liquid hydrocarbon fraction with hydrogen at elevated temperature and superatmospheric pressure, optionally in the presence of a catalyst. For example, the hydrogenation may comprise hydrotreatment, hydrocracking or hydrodesulfurisation. Hydrocracking tends to have the highest demand for hydrogen but is often the preferred procedure.

The hydrogenation may involve more than one hydrogenation step, for example the hydrogenation may comprise a first hydrogenation step followed by fractionation of the first hydrogenation product and further hydrogenation of one or more of the fractions so produced. Further processing steps such as e.g. cracking may be interspersed between hydrogenation steps.

In the next step, hydrogenated material recovered from the hydrogenation, and which may comprise a part or all of the product of the hydrogenation step, is fractionated to produce a gaseous fraction containing methane and at least one liquid hydrocarbon stream. The fractionation may be carried out in known manner and employing well-known conditions. The gas may include $C_2$, $C_3$ and possibly $C_4$ hydrocarbons but it may be preferred to recover at least the $C_3$ and $C_4$ components as a separate cut e.g. for use as LPG and bottled gas. The gas may also include unreacted hydrogen and additionally hydrogen sulfide if the liquid hydrocarbon fraction which is hydrogenated contains sulfurous materials.

The fractionation may be operated in one or more steps and to produce a single liquid hydrocarbon product or a plurality of liquid cuts, e.g. suitable for use as or in the production of motor spirits (gasoline), aviation turbine fuel, aviation gasoline, vaporising oil, kerosine, diesel oil, heavy diesel oil, etc.

Where the liquid hydrocarbon fraction to be hydrogenated has been produced by distillation, e.g. as in the atmospheric and/or vacuum distillation of oil, the fractionation of the hydrogenation product may be effected by recycling the product to said distillation. Alternatively, it may be fractionated in a separate step. Where it is recycled, the recovery of the methane-containing gas will generally be effected by a degassing step prior to recycling.

Where there is more than one hydrogenation step, it will generally be desirable to recover methane-containing gas from the product of each hydrogenation.

In accordance with the invention, at least a part and preferably all of the hydrogen requirement of the hydrogenation step is obtained by steam-reforming methane-containing gas recovered from the hydrogenated material. The entire gaseous product of the hydrogenation may be steam reformed, if desired, but it may be treated first e.g. to separate specific fractions which may be required as premium products, as mentioned above.

If insufficient gas is available from the hydrogenation to satisfy the hydrogen requirements of the hydrogenation, the deficiency may be resolved by additionally steam reforming at least a portion of the lighter liquid hydrocarbons produced by hydrogenation, e.g. hydrocarbons having 4 to 7 carbon atoms or a suitable naphtha fraction.

It is preferred to remove any sulfur-containing gases prior to steam reforming. It may also be desired to remove any unreacted hydrogen; however, the increased heat burden on the steam reformer from retaining some or all of the hydrogen is tolerable because low grade fuel is used. The feed to the reformer may also include methane-containing gas produced as a direct product of the separation step, e.g. gas from a distillation, pyrolysis or cracking step employed in the separation. The steam reforming operation may be effected in known manner and employing well-known conditions.

To maximise hydrogen production and to eliminate carbon monoxide which interferes with hydrogenation catalysts it is preferred to encourage the CO shift reaction in known manner, e.g. by spraying water into the gas recovered from the reformer, and the carbon dioxide may then be removed from scrubbing, also in known manner.

Any carbon monoxide still remaining in the reformate may be eliminated by methanation and steam in the reformate may be condensed out.

Hydrogen for the hydrogenation step may then be provided from the remaining gas which will comprise primarily hydrogen and some unreacted methane.

As indicated above, the fractionation of the hydrogenated material may include recycling it to a distillation train from which is derived a gaseous fraction and liquid hydrocarbon fraction to be hydrogenated. By such recycle, a wide degree of control of the nature of the desired net liquid product from the fractionation may be achieved.

In accordance with the invention, the heat for the steam reforming is provided by at least partly immersing the reformer reactor vessel (which term is to be understood to include a single reactor vessel or a plurality of such vessels, e.g. catalyst-packed reactor tubes) in a fluidised bed of finely divided solid material which is heated by combustion of a fuel provided from the residue produced by the separation step. The process can be adapted so that all the fuel requirements are provided by said residue, which may be solid, semisolid or liquid in nature. This may be achieved e.g. by control of the separation step to produce the required amount of residue.

Where the residue is an ash-containing solid, it is provided in particulate form, preferably having a maximum dimension not exceeding 6 mm, and more preferably with an average particle size of 0.25 to 1.0 mm, and is normally supplied to the bottom of the bed, the ash being removed either continuously or discontinuously. The fuel may be fed in dry powder form or as a slurry e.g. in water. Where the fuel is fusible, e.g. as in the case of oil-derived residues, it may be first melted and then fed to the fluidised bed in molton form.

Where the fuel is ash-less or the ash formed is insufficient to form the fluidised bed, inert material may be added to provide or contribute to the formation of the fluidised bed. Any suitable inert material may be used and examples are alumina and sand. If desired, dolomite or limestone may be included in the bed to reduce the level of oxides of sulfur in the flue gas where sulfur-containing fuels are employed. The inert material and/or limestone or dolomite should ideally have a maximum particle dimension of 6 mm and an average particle size in the range 0.25 to 1.0 mm.

Where fuels containing high metal contents and in particular heavy oil or oil residue fuels containing vanadium are used, it may be advantageous to introduce magnesium in the form of dolomite to suppress hot metal erosion due to vanadium, particularly in the region of the expander gas turbine.

The bed is fluidised by gas, normally the oxidant gas, e.g. air, required for the combustion, and is generally supplied from below.

It is desirable to operate the fluid bed combustor with excess air, preferably in the range 10 to 100% and most preferably in the range 20 to 50% excess of stoichiometric. It is also possible to operate the combustor with a deficiency of air with provision for burning off combustible gases by the addition of air after the fluid bed combustor.

The invention is now described in greater detail with reference to preferred embodiments thereof and with the aid of the attached drawings in which.

Figure 1:
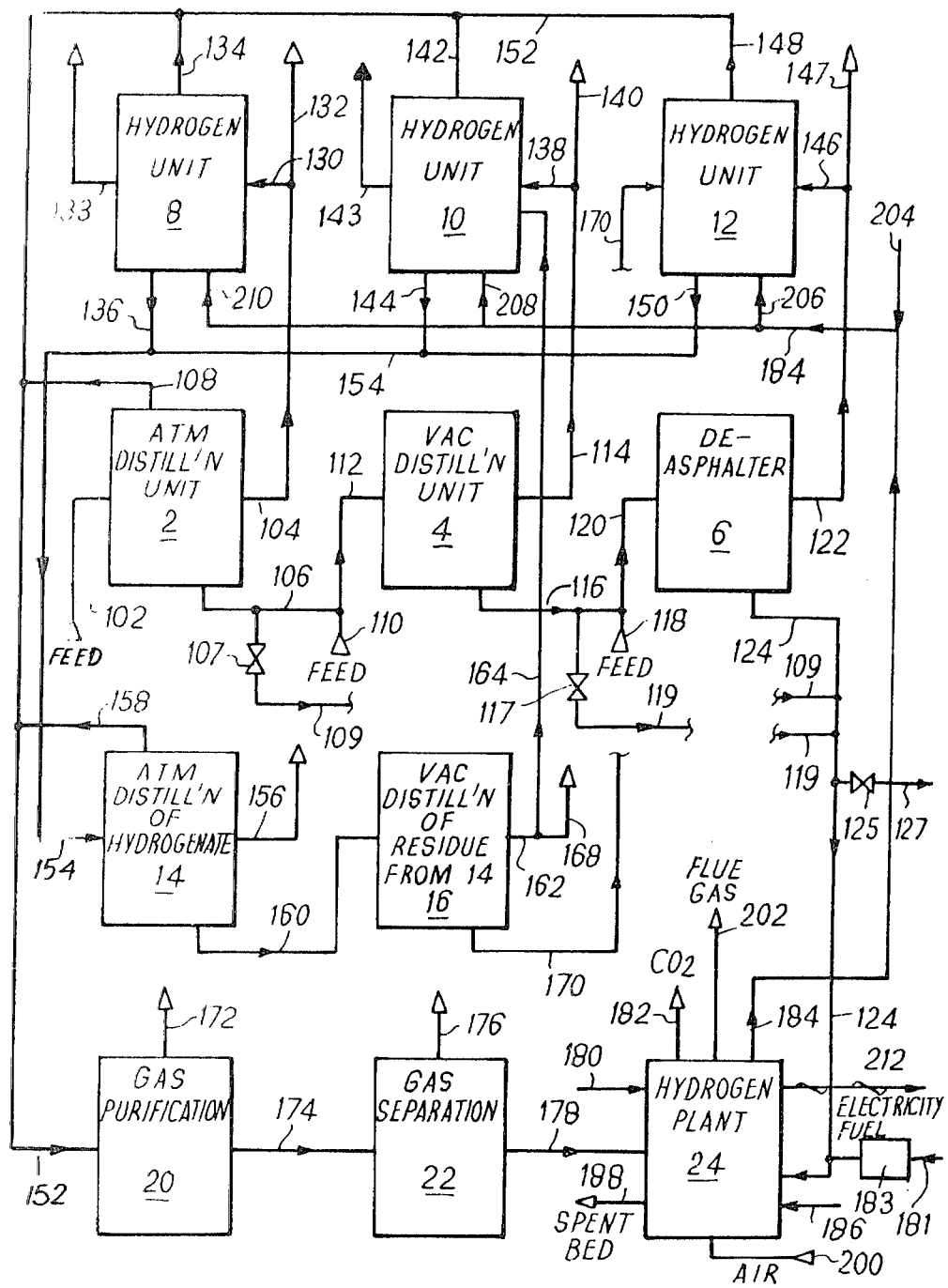
FIG. 1 is a block flow diagram of an oil processing plant embodying the process of the invention.
Figure 3:
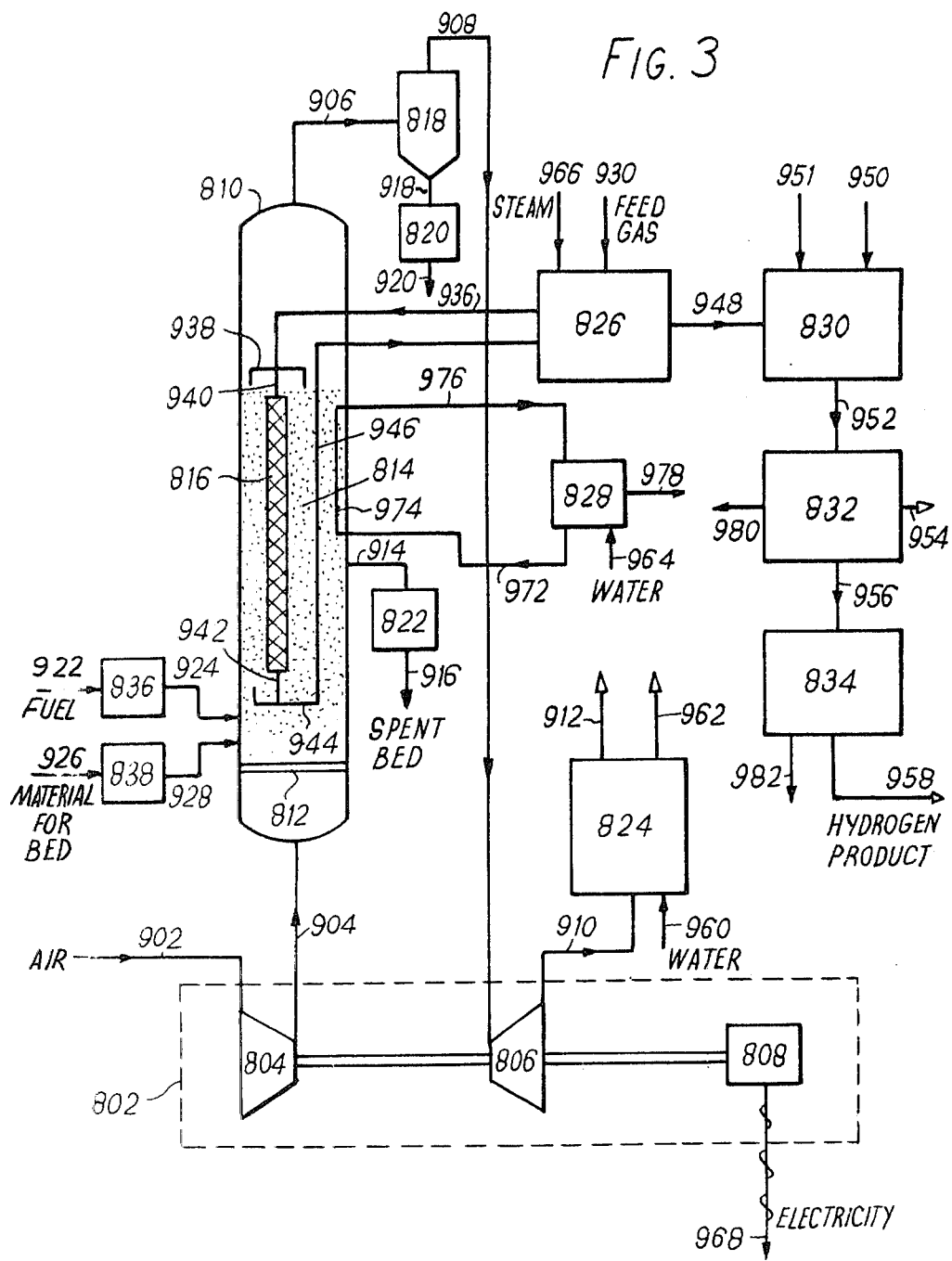
FIG. 3 illustrates in more detail the steam reformer/fluidised bed combustor arrangement employed in the plants of FIGS. 1 and 2.

Referring to FIG. 1 of the drawings, reference numeral 2 is an atmospheric distillation unit, 4 is a vacuum distillation unit and 6 is a vacuum residue processing unit such as a solvent de-asphalter. 8, 10 and 12 are hydrogenation units for treating, respectively, atmospheric distillates, vacuum distillates and solvent refined product from vacuum residue processing unit 6. 14 is an atmospheric distillation unit for processing hydrogenated products from hydrogenation units 8, 10 and 12, and 16 is a vacuum distillation unit for treating the residue from the atmospheric distillation unit. 20 is a refinery gas purification plant, 22 is a gas separation unit and 24 is a hydrogen production plant incorporating a residue-fired fluid bed reformer and the arrangement of which is shown in more detail in FIG. 3.

Processing unit 6 could also be a vis-breaker or a coker. Other units such as catalytic reformers and catalytic crackers (not shown) may be incorporated in the overall processing unit which as a result would involve additional process streams not shown in the diagram. It will also be understood that variations in the illustrated flow arrangements may be made.

It will also be understood that the units referred to above incorporate columns, vessels, pumps, heaters, etc, as is well known in the art, and that subsidiary process and service connections are not shown. It is also to be understood that the pipelines shown may represent a single pipeline or a plurality of pipelines in parallel.

The feed to the plant may comprise crude oil supplied through line 102 and/or a heavy oil or oil residue supplied through line 110 and/or line 118. Feed supplied through line 102 is separated in atmospheric distillation unit 2 into a gaseous fraction removed overhead through line 108, atmospheric distillate which is removed through line 104 and a residue which is removed through line 106. Provision is made for supply of some or all of this residue, if desired, as fuel for the hydrogen plant 24 via valve 107 and pipelines 109 and 124.

The remainder, if any, of the residue in line 106 and/or fresh feed supplied through line 110 is transferred via line 112 to vacuum distillation unit 4 where it is separated into a vacuum distillate removed in line 114 and a residue which is removed in line 116. There is provision for supplying some or all of this residue, if desired, as fuel for the hydrogen plant 24 via valve 117 and lines 119 and 124.

Any remainder of the residue in line 116 and/or any fresh feed to the plant supplied through line 118 is transferred via line 120 to the vacuum residue processing unit 6 which, in the arrangement illustrated, is a solvent de-asphalting unit. Solvent de-asphalted product which has also been substantially stripped of mineral matter and its metal content such that it is a suitable general hydrogenation feed, is withdrawn from the unit via line 122 and the asphalt containing residue is withdrawn via line 124. Some of the residue material in line 124 may be withdrawn via a valve or suitable control device 125 and line or transfer system 127. This residue may be used as a low grade fuel or asphalt or may be blended with light oil to produce a heavy fuel oil. The residue in line or alternate transfer system 124 is supplied as fuel to hydrogen plant 24.

Atmospheric distillate in line 104 may be passed via line 132 for disposal as product or via line 130 to hydrogenation unit 8. Hydrogenated material from 8 may be disposed as product via line 133 and/or may pass via lines 136 and 154 for distillation in unit 14. Surplus gas from unit 8 leaves via lines 134 and 152.

Vacuum distillate in line 114 may pass via line 140 for disposal as product or via line 138 to hydrogenation unit 10. Hydrogenated material from 10 may pass via line 143 for disposal as product and/or via lines 144 and 154 for distillation in unit 14. Surplus gas is removed via line 142.

De-asphalted oil in line 122 may pass via line 147 for disposal as product and/or via line 146 to hydrogenation unit 12. Hydrogenated material from 12 will normally be passed via lines 150 and 154 for distillation in unit 14 but some may be withdrawn as product (now shown). Surplus gas is recovered via line 148.

The hydrogen requirements for hydrogenation units 8, 10 and 12 are provided at suitable pressure from line 184 via lines 210, 208 and 206, respectively. The source of the hydrogen is described below.

The hydrogenated material collected in line 154 from units 8, 10 and 12 is passed to atmospheric distillation unit 14 where it is fractionated into one or more liquid fractions recovered in line 156, stripped gas which is recovered via line 158 and atmospheric residue which leaves via line 160 and is passed to vacuum distillation unit 16. The liquid fraction or fractions from unit 16 are recovered in line 162 and may be disposed of as product via line 168 and/or recycled for further hydrogenation in hydrogen unit 10 via line 164. Residue from unit 16 is passed back to hydrogenation unit 12 via line 170.

In this way, the distillates from units 2, 4 and 6 may be recirculated and upgraded by hydrogenation and subsequent distillation and further recirculation to produce enhanced lower molecular weight product ultimately recovered from 133, 143, 156 and/or 168.

The gas from distillation units 2 and 14 and hydrogenation units 8, 10 and 12 is collected in line 152 and passed to gas purification unit 20 in which undesirable constituents such as hydrogen sulphide and ammonia are removed via line 172. Purified gas is recovered in line 174 and passed to optional separation unit 22 which separates the gas into two or mre fractions. Specific fractions such as hydrogen and/or propane and/or butane may be removed via line 176, which may be a plurality of product pipelines, and may be disposed of as product or recycled to specified process e.g. the $H_2$ into line 204. The remaining gas comprising the methane values in the gas stream and possibly other light hydrocarbons, is passed via line 178 to hydrogen plant 24.

This plant comprises a steam reformer heated by a fluidised bed combustor, as more particularly illustrated in FIG. 3. The arrangement is described in more detail below. Fuel for this plant enters via pipeline or conveying system 124 and adsorbent and/or inert material to form the bed is provided by a transport system 186. Combustion air enters via duct 200 and process water via line 180. Flue gas exhausts through duct 202, carbon dioxide is vented via duct 182 and spent adsorbent and/or fluid bed fines are disposed of via transport system 188. Product hydrogen is recovered via line 184 for supply to units 8, 10 and 12, and may be supplemented, if required, by hydrogen supplied through line 204 from another source.

If insufficient fuel is available from the residues supplied through line 124, additional fuel such as coal or lignite may be supplied via transfer system 181 and control device 183.

Referring now to FIG. 3, 802 is a as turbine-driven combustion air compressor and power generation unit including an air compressor 804, a hot gas expander 806 and an alternator 808. The machine is shown as a single fixed shaft machine but may also be a single split shaft machine or a machine having more than one shaft for air compression and hot gas expansion, and may also be split into a number of machines, for example one expander driving the air compressor and a separate expander driving the alternator. In all cases, the drive shaft to the compressor and/or alternator may incorporate gearboxes.

810 is a pressurised fluid bed combustor/gas reformer having a distribution grid 812, a fluid bed 814 and a plurality of catalyst-filled reformer tubes 816 (for simplicity, only one is shown). 818 is a dust remover cyclone or set of cyclones or an alternate filtration device, 820 and 822 are ash removal and pressure let-down devices and 824 is a flue gas waste heat boiler. 826 is a set of heat exchangers for feed gas preheating and hot synthesis gas cooling and 828 is a boiler. 830 is a shift reactor system, 832 is a carbon dioxide scrubbing system and 834 is a methanation system. 830, 832 and 834 are designed in accordance with well-established principles for the design of such units for hydrogen plants. 836 and 838 are devices or systems for compressing and feeding, respectively, fuel for the fluidised bed combustor and crushed limestone and/or dolomite and/or inert material such as sand or alumina for the fluidised bed.

Combustion air entering the system through pipeline 200 (FIG. 1) is drawn through duct 902 into the air compressor 804 in which it is compressed to between 5 and 40 Bar, and preferably to between 12 and 25 Bar. Intercooling during compression may be employed but after-cooling is not desirable. The compressed air is then passed via pipeline 904 to the base of the fluid bed combustor 810.

Residues provided through line 124 (FIG. 1) connecting with line 922 are fed at a controlled rate and under pressure to the fluidised bed by feeding system 836. The feeding system may comprise a heater and pump in the case of fusible oil residues or, where the residues are infusible, e.g. as in the case of the char formed in the arrangement of FIG. 2 below, the system may comprise a water slurrying device and pumping system or a dry powder feed sysem such as manufactured by Petrocarb or some suitable alternate device. The fuel from the feeding device 836 passes via pipeline 924 to the fluid bed combustor 810. Pipeline 924 may be a single line or more preferably a number of lines in parallel. The fuel is shown as fed into the fluid bed 814 above the distribution grid 812 but the feed point or points may be incorporated with the distribution grid 812. It is possible to feed fuel at many points in the fluid bed 814; however it is preferable to feed the fuel at least between the grid 812 and the lower manifold 944 (referred to below) and preferably close to the grid 812.

Inert material such as sand or alumina to produce or augment the necessary fluid bed 814 and/or a sulphur adsorbent such as limestone or dolomite supplied by transport system 186 (FIG. 1) is fed via feed duct 926 to feeding device 838 which may be a water slurrying device and pumping system or a dry powder feed system or some suitable alternate device. The inert material and/or adsorbent is fed via pipeline 928 to fluidised bed 814. The location of feed pipe 828 is not critical but ideally is above and adjacent to grid 812. It is possible to integrate feed devices 836 and 838 to feed a mixture of fuel and inert and/or adsorbent or to slurry the inert and/or adsorbent in molten oil residues.

The grid 812 may be a proprietory design or a heat resistant metal plate which may be in segmented form to allow for expansion and contraction, in which a series of bubble-cap type distributors or alternate gas distribution devices are fixed. Even distribution of air through the distributors and the bed requires a pressure drop across the distributors in the order of 0.05 to 0.10 Bar.

For any given pressure, the range of air and flue gas velocities in the bed for a given average particle size is well-established and it is generally desirable to operate with a velocity in the lower range of available velocities in order to ensure minimum erosion of the reformer tubes 816, manifolds and connecting lines and risers 942, 944 and 946. From the velocity and the quantity of combustion air required to provide the necessary heating, the cross-sectional area of the bed can be determined.

The depth of the bed may range from 2 to 14 meters or more. The preferred depth for vertical cylindrical and un-finned reformer tubes is 7 to 12 meters with the tubes occupying the upper 6 to 11 meters of the bed. The fluid bed consists predominately of ash from the fuel and/or deliberately added inert material and/or dolomite or limestone adsorbent and in order for the bed height to be held constant, ash is drawn off from the bed through duct 814 to draw-off device 822. The draw-off may be constant or intermittent and may be based on the overflowing of the bed into the duct 914 or it may be controlled by a bed level sensing device which may be designed to detect the pressure drop across the bed and by inference the bed height. The draw-off device draws off ash under pressure and may let it down through a system of lock-hoppers using well-established designs or through one or more rotary type valves or some suitable alternate device. De-pressurised ash and/or inert material and/or spent adsorbent is discharged via duct 916 to duct 188 (FIG. 1).

The fluid bed may be of the simple up-flow type as illustrated or it may incorporate a spouting device with two separate and distinct upward velocity zones.

It is preferred to operate the bed with an excess of air ranging between 20% and 50% above stoichiometric. However it is possible to operate above 50% excess air if the plant is required to produce a surplus of energy in the form of mechanical energy from the turbine 806 and/or in the form of steam. It is also possible to operate with a deficiency of air with the combustion of carbon monoxide and possibly hydrogen formed in the bed being carried out by adding more combustion air above the bed 814 or subsequent to the combustor 810. It is generally not desirable for metallurgical reasons to operate the bed such that there are transitions between an excess and deficiency of combustion air.

The temperature of the fluid bed 814 is controlled at a fixed value and in the range of 750° to 1100° C. but more preferably within the range of 850° to 1000° C. generally by primary control of the fuel feed rate and secondary control of combustion air flow to minimise the likelihood of carbon formation in reformer tubes 816 or overheating of the connecting tube headers and risers 938, 944, 946. This temperature range also allows the use of well-established alloys such as Incalloy and HK40 for tubes support etc and also the effective retention of sulphur by limestone or dolomite adsorbent if sulphur removal is required.

Hot fuel gases leave the combustor 810 through the duct 906. These hot gases also contain fine dust in suspension and the mixture passes through the dust removal system 818 which may consist of cyclones and/or filtration systems but generally consists of primary and secondary cyclone systems which ensure the removal of the greater part of the entrained dust. The maximum size of dust particle leaving the secondary cyclone should be about 10 micron so as not to unduly interfere with the operation of the hot gas expander 806. Ash is removed from separator 818 via pipe 918 to the ash discharge device 820 which may be a system of lock-hoppers and/or rotary valves or similar alternate device. De-pressurised ash is removed via pipeline 920. Pressurised and cleaned hot gas from separator 818 passes via duct 908 to the expander turbine 806 in which the exhaust gases are let down to substantially atmospheric pressure and then pass through duct 910 to a waste heat boiler 824 and thence via duct 912 to atmosphere. Suitably pressurised feed water is admitted via pipeline 960 to the boiler 824 which may incorporate a preheater and superheater and the resultant produced steam leaves via pipeline 962.

Methane-containing gas from line 178 is supplied via line 930 to the heat exchange system 826 where a controlled amount of steam is added from pipeline 966. In 826, the methane/steam mixture is heated to about 500° C. before passing via pipeline 936 into the pressurised combustor 810 where it is distributed by the header system 938 and a series of connecting tubes 940 to catalyst filled reformer tubes 816 (one only is shown). These tubes may be of current state of the art design i.e. vertical, cylindrical, plain tubes packed with a suitable proprietary steam reformer catalyst or they may be finned tubes or abnormally shaped tubes which would operate satisfactorily due to the reduced stresses on the tubes. The methane and any heavier hydrocarbons associated with the methane are substantially reformed in the tubes to hydrogen and carbon monoxide and exit through connecting stubs 942, bottom collection header 944 and thence upwardly through riser 946 and through the shell of the combustor 810 to the heat exchange system 826. The riser 946 and the feed line 936 together with the headers 938 and 944 incorporate suitable arrangements for differential expansion and contraction due to the temperature variations during start-up operation and shut-down of the combustor. The tubes are suitably supported using for example a high temperature metal support grid above the tubes supported from the walls of the combustor 810 using tie rods to support the upper tube header 938, the inlet pipe 936 and the riser 946.

In heat exchange system 826, the hot reformate is cooled to about 500° to 650° C. and is then transferred via line 948 to shift reactor system 30 where it is mixed with water and/or steam to further cool the gas to about 360° to 380° C., and then passed over a high temperature shift catalyst. It is then mixed with additional water and/or steam to further cool the gas to about 210° C. after which it is passed over a low temperature shift catalyst to convert the bulk of the carbon monoxide by reaction with water to carbon dioxide and hydrogen. The product gas passes via line 952 to the cooling and carbon dioxide scrubbing system 832 where the reformed and shift-reacted gas is cooled and scrubbed to remove carbon dioxide. The heat content of the entering gases is generally sufficient to provide the necessary heat for stripping the carbon dioxide from the scrubbing liquid used for the process, namely hot carbonate solution. Carbon dioxide is withdrawn via line 954 and condensate via line 980.

Gas recovered from the cooling and scrubbing unit 832 is passed via line 956 to methanation unit 834 in which any remaining carbon monoxide is converted to methane by known means. The unit may incorporate a separately fired heater or may (by means not shown) employ heat from the hot gas streams in lines 910 and/or 958. The gas is then further cooled in the methanation unit and condensate is recovered via line 982. Product hydrogen is recovered via line 958 which connects with line 184 (FIG. 1) for passing the hydrogen to the hydrogenation units 8, 10 and 12.

The steam for the steam reforming may be provided from line 962. If further steam is required for the steam reforming and/or for other uses e.g. power generation, it may be provided from line 978 from ancillary boiler 828. Feed water at a suitable pressure is supplied to this boiler via line 964 and water is circulated via lines 972, 974 and 976 through the fluid bed 814 where it is heated to produce superheated steam or a mixture of water and steam. Steam generated in this boiler is recovered via line 978.

If desired, feed water for boiler 828, and also boiler 824, may be preheated in the cooling and carbon dioxide scrubbing unit 832.

By means of the arrangement illustrated in FIG. 3, hydrogen may be produced at about 20 Bar with a purity of up to 98%. If the pressure is increased to 40 Bar, the product gas will contain about 85 to 90% hydrogen. However, as the purity of the hydrogen is not critical for the hydrogenation reactions in hydrogenation units 8, 10 and 12, such lower purity is acceptable and operating at this higher pressure reduces compressor and compression costs.

With the combustor 810 running at its preferred pressure range, expander turbine 806 will produce energy in excess of that required to power compressor 804. Recovery of the surplus energy plus speed control of the turbine 806 may be achieved by generating power in alternator 808 which supplies electric power via cable 968/212. (FIG. 1)

Figure 2:
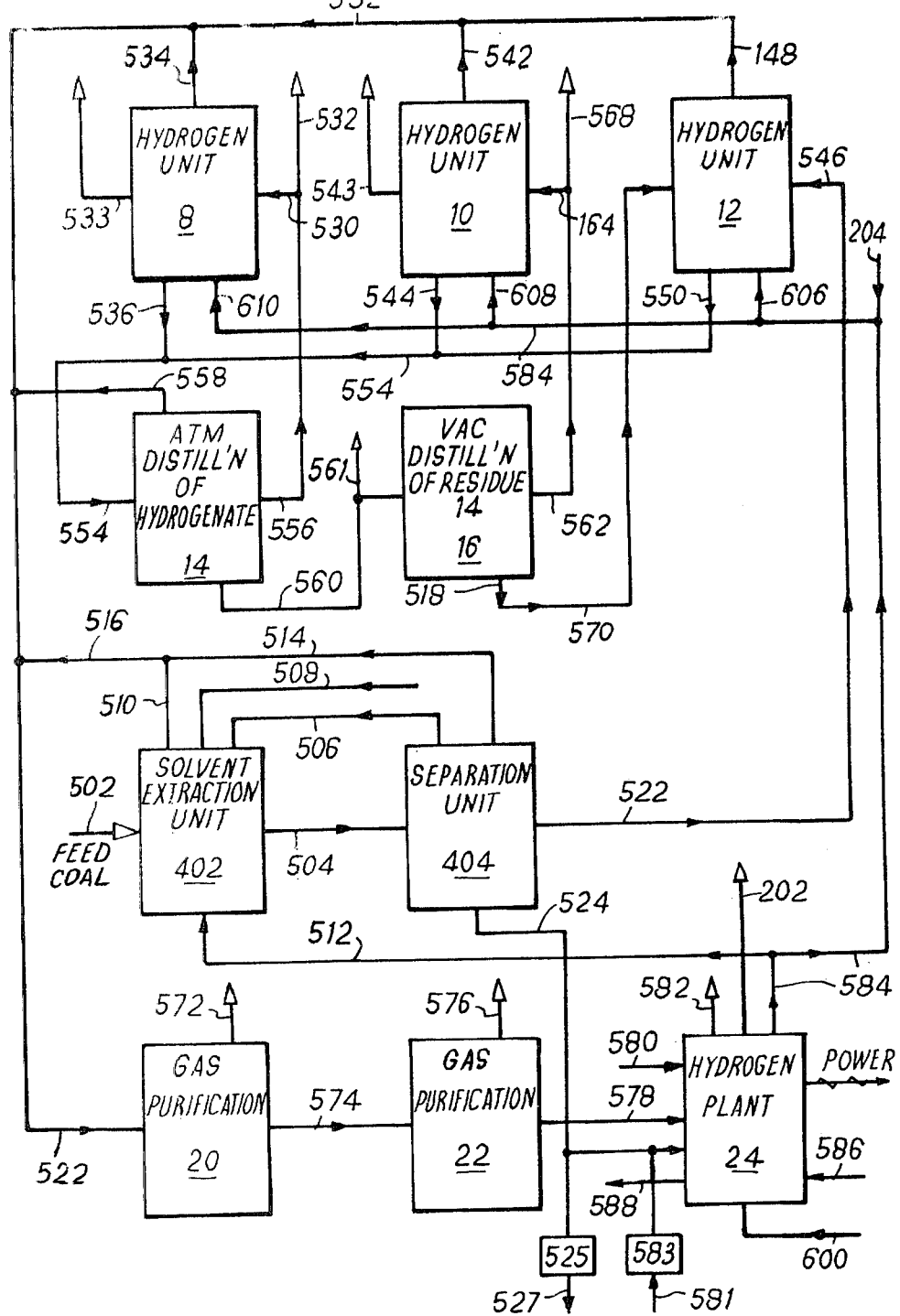
FIG. 2 is a block flow diagram of a plant for the production of oil from coal and embodying the process of the invention.

A coal-based synthetic oil plant incorporating the process of the invention is illustrated in FIG. 2 in which reference numeral 402 is a solvent extraction unit designed to operate a sub-critical solvent extraction process, a super-critical solvent extraction process or a solvent contacting process combined with hydrogenation, i.e. H-coal process. 4 is a separation unit for separating the product from 402 into a liquid extract (possibly in solution with a solvent ) which is suitable for hydrogenation, and a solid residue comprising mineral matter and coal char. It will be understood that units 402 and 404 could be replaced by a pyrolysis or carbonisation plant. As in FIG. 1, 8, 10 and 12 are hydrogenation units, 14 is a unit for the atmospheric distillation of hydrogenated material recovered from units 8, 10 and 12, and 16 is a unit for the vacuum distillation of residue from unit 14. Similarly, units 20, 22 and 24 are, respectively, a gas purification plant, gas separation plant and hydrogen plant.

It will be understood that, as in the case of the plant illustrated in FIG. 1, other units such as catalytic reformers and catalytic crackers may also be included, and that the units illustrated incorporate vessels, pumps, heaters etc in well known manner. Variations in the flow arrangements are possible and the lines shown may represent a single pipeline or a plurality of pipelines arranged in parallel.

Suitably prepared coal is fed to solvent extraction unit 402 by means of transportation system 502 and solvent is provided through line 508 and/or 506. Where hydrogenation is required, hydrogen may be provided via line 512. Any surplus gas is vented via lines 510 and 516 to line 552.

The mixture of dissolved coal, solvent, undissolved char and mineral matter is passed by means of transport system 504, which may be a lock hopper, pipeline or suitable alternate device, to separation unit 404. In this unit, generally by either pressure reduction and/or heating, additional gas is liberated and removed via line 514. Surplus solvent is recovered via line 506 and recycled to solvent extraction unit 402, and coal liquids, possibly still containing some solvent, are recovered via line 522 and passed via line 546 to hydrogenation unit 12.

Hydrogenated material produced in unit 12 exits via line 550 and is passed via line 554 to distillation unit 14. All the lines shown in association with units 8, 10, 12, 14 and 16 have the same function as the corresponding lines of FIG. 1 having the same last two digits in the reference numeral, with the exception that distillates in lines 532, 533, 543 and/or 568 may be recycled to solvent extraction unit 402 via line 508. Further, in some cases residue from distillation unit 14 may be recovered through line 561 as product, and the vacuum distillation unit 16 may be omitted.

Gas from hydrogenation units 8, 10 and 12, distillation unit 14, solvent extraction unit 402 and/or separation unit 404 is collected in line 552 and passed to gas purification unit 20, gas separation unit 22 and hydrogen plant 24, all of which operate in the same manner as in the arrangement described with reference to FIG. 1.

However, in this plant, the hydrogen production unit 24 is fired with coal residues from separation unit 404 and supplied through transport system 524. If desired, part of the residue may be disposed of via control device 525 and transport system 527. Likewise, if insufficient residue from separation unit 404 is available to fuel hydrogen plant 24, additional fuel may be provided via transport system 581 and control device 583.

Thus, in this plant, feed coal provided through transport system 502 is treated in unit 402 and separated in unit 404 into a liquid product and a residue. The liquid product is hydrogenated in 12, hydrogenated material is fractionated in 14 and 16 and liquid streams recovered from these units are further hydrogenated in hydrogenation units 8 and 10. Hydrogenated material from 8 and 10 is recycled to distillation units 14 and 16 and the desired products are recovered through lines 532, 533, 543 and/or 568. The gas recovered from units 8, 10, 12, 14, 402 and/or 404 is steam reformed in hydrogen plant 24 to produce the required hydrogen for plants 8, 10 and 12. The fuel-containing residues from separation unit 404 provide the fuel for the fluidised bed combustor of hydrogen plant 24 which in detail is as described above with reference to FIG. 3 but with the fuel feed supplied to line 922 being coal residues provided via transport system 524.

EXAMPLE 1

Using the plant described and illustrated in FIGS. 1 and 3, 26,178 tonnes/day of a blended atmospheric residue oil derived from middle east crude oils is supplied through line 110 to vacuum distillation unit 4 where it is separated into a distillate all of which is hydrogenated in hydrogenation unit 10 and a residue which is recovered through line 119/124. Liquid hydrogenate from 10 is distilled in atmospheric distillation unit 14 to yield light naphtha, heavy naphtha, kerosine and diesel cuts, and a residue which is distilled in vacuum distillation unit 16 to produce a distillate which is recycled to hydrogenation unit 10 and a residue. Gas from the hydrogenation is recovered in line 142 and, after treatment in 20 and 22 to remove ammonia and $H_2S$, is passed to hydrogen generation plant 24 from which the hydrogen product is returned in lines 184 and 208 to the hydrogenation unit 10. Units 2, 6, 8 and 12 are not used.

The process details are as follows.

| Vacuum gas oil recovered in line 114 | |
|---|---|
| A Flow rate | 16492 tonnes/day |
| B Boiling range: IBP | 347° C. |
| C 50% | 450° C. |
| D EP | 505° C. |
| E Sulphur content | 1.8% w/w |
| F Nitrogen content | 0.1% w/w |

| Vacuum residue recovered in line 119/124 | |
| --- | --- |
| G Flow rate | 9686 tonnes/day |
| H A.P.I. gravity | 5.9 |
| H Sulphur content | 4.5 % (wt/wt) |
| K Ni and V content | 130 ppm |

| Composition of gas in line 142 (weight % of feed flow in line 110) | |
| --- | --- |
| $H_2S$ and ammonia | 2.04% |
| M Methane, ethane, propane, butane and light naptha | 5.63% |

| Hydrogen in line 184/208 | |
| --- | --- |
| N Flow rate | 419 tonnes/day |

| Feed to Hydrogen Plant | |
| --- | --- |
| P Vacuum residue in line 124: | 910 tonnes/day |
| R Dolomite | 350 tonnes/day |
| S Steam at 25 Bar | 7210 tonnes/day |

| Product streams recovered from Atmospheric distillation unit 14 | |
| --- | --- |
| T Light naphtha | 434 tonnes/day |
| V Heavy naphtha | 1145 tonnes/day |
| W Kerosine | 6465 tonnes/day |
| X Diesel | 7603 tonnes/day |

584/606. Liquids from the hydrogenation plant are passed in line 550/554 for atmospheric distillation in 14 to produce two liquid products, recovered through lines 556 and 560 respectively. Gas from 402 and 14 joins the gas from hydrogenation unit 12 in line 552 for passing to hydrogen plant 24. Char recovered from separation unit 404 in line 524 is passed to the hydrogen plant 24 as fuel for the fluid bed combustor. Units 8, 10 and 16 are not used. In this Example, about 75 tonnes/day of gas is purged through line 176.

The process details are as follows.

| | | |
| --- | --- | --- |
| AA | Feed coal in line 502: Flow rate (ash and moisture free) | 23,650 tonnes/day |
| CC | Char in line 524, production rate (ash and moisture free) | 13,782 tonnes/day |
| DD | Total hydrocarbon gas in line 552 including 44.1 tonnes/day $H_2$ | 1,203.6 tonnes/day |
| EE | Rate of consumption of char in hydrogen plant 24 | 1,692 tonnes/day |
| FF | Net surplus char available as product via line 527 (including 40% ash) | 21,278 tonnes/day |
| | Liquid fractions available as product from distillation unit 14: | |
| GG | in line 556/532 IBP 200° C. fractions | 2,784 tonnes/day |
| HH | in line 560 200° C. + fraction | 4,923 tonnes/day |

The following illustrates the operating details of steam reformer/fluid bed combustor described and illustrated in FIG. 3 and employed in hydrogen plant 24 of Example 2.

| | | |
| --- | --- | --- |
| JJ | Char in line 924: calorific value | 5,054 Kcal/kg |
| KK | ash content | 40% |
| LL | feed rate | 1,692 tonnes/day |
| MM | average particle size | 0.6 mm |
| | Feed gas in line 930 (C/H ratio is 3.8/1 wt/wt) | |
| NN | pressure | 25 Bar |
| PP | feed rate | 1128.3 tonnes/day |
| RR | Number of combustors 810 | 4 |
| SS | Inside diameter of each combustor | 5.8 meters |
| TT | Number of reformer tubes in each combustor | 500 |
| VV | Outside diameter of reformer tube | 100 mm |
| WW | Length of reformer tube | 9.15 meters |
| XX | Depth of fluid bed | 11.0 meters |
| ZZ | Air flow in line 904: flow rate | 565,000 $Nm^3$/hr |
| AAA | pressure | 20 Bar |
| BBB | Steam/methane ratio in 936 | 4.0 |
| CCC | Hydrogen product in line 958: flow rate (as 100% hydrogen) | 441 tonnes/day |
| DDD | purity (minimum) | 95% hydrogen |
| EEE | pressure | 18 bar |
| FFF | Adsorbed power of air compressor 804 | 95,000 Kw |
| GGG | Power generated in turbine 806 | 140,000 Kw |
| HHH | Net power available from alternator 808 in line 968 | 45,000 Kw |
| JJJ | Power required for hydrogenation plant in Example 1 | 45,000 Kw(approx) |

EXAMPLE 2

Using the plant described and illustrated in FIGS. 2 and 3, coal in powdered form and provided through line 502 is solvent extracted by supercritical solvent extraction techniques in 402 and the coal liquids thereby produced are separated in 404 and hydrogenated in hydrogenation unit 12. Gas from 12 is recovered in line 148/552 and passed to the hydrogen plant 24 and hydrogen generated from this gas is returned to 12 in line This steam reformer/fluid bed combustor is employed in the arrangement of FIG. 1, by replacing char feed by a supply of vacuum distillation residue provided through line 119/124 (FIG. 1).

In both Example 1 and Example 2, water is injected into the fluidised bed. In Example 2, it is provided by feeding the char as 50/50 wt/wt slurry in water. In Example 1, an equivalent amount of water is added with the dolomite. Where the fluidised bed is pressurised, injecting water increases the power available from the flue gas and is a valuable means for disposing of waste water from processes involved in the extraction of the residue used to fuel the bed e.g. colliery waste water or refinery oily water waste.

I claim:

1. A process which comprises the steps of separating a fossil-based feedstock containing a substantial proportion of high molecular weight organic polycyclic components and also mineral and/or metallic components to provide (a) a residue containing fuel values and substantially all of said mineral and/or metallic components and (b) a liquid hydrocarbon fraction; reducing the average molecular weight of said liquid hydrocarbon fraction by hydrogenation; and fractionating hydrogenated material thereby obtained to form a gaseous fraction containing substantially all the methane in the hydrogenated product and at least one liquid hydrocarbon stream; and providing hydrogen for said hydrogenation by steam reforming a methane-containing gas provided from said gaseous fraction, the reforming being effected at elevated temperature in a reactor vessel which is at least partly immersed in a fluidised bed of finely divided solid material which is heated by combustion of a fuel provided at least in part from said residue of said separation step.

2. A process as claimed in claim 1 in which the feedstock comprises an oil and the separation step comprises distillation and solvent deasphalting, coking or visbreaking the distillation residue.

3. A process as claimed in claim 1 in which the feedstock comprises coal, lignite or peat and the separation step comprises solvent extraction with recovery of the solvent for recycle.

4. A process as claimed in claim 1, wherein the hydrogenation and steam reforming steps are conducted at superatmospheric pressure and the fluidised bed is under superatmospheric pressure, and the power for pressurisation of these steps and for pressurising the fluidised bed is provided by expansion through an expansion engine of the flue gas from the combustion of the fuel.

5. A process as claimed in claim 1 wherein additional hydrogen for the hydrogenation is provided by steam reforming liquid hydrocarbon product of the hydrogenation.

6. A process as claimed in claim 4 wherein waste water from a process employed in the extraction of the residue is injected into the fluidised bed.

* * * * *

UNITED STATES PATENT AND TRADEMARK OFFICE
CERTIFICATE OF CORRECTION

PATENT NO. : 4,308,128
DATED : December 29, 1981
INVENTOR(S) : Donald R. Cummings It is certified that error appears in the above—identified patent and that said Letters Patent is hereby corrected as shown below:

On the title page, insert Foreign Application Data as follows:

-- Aug. 2, 1979 (GB)   Great Britain            7926932 --.

Signed and Sealed this

Sixteenth Day of March 1982

[SEAL]

Attest:

Attesting Officer

GERALD J. MOSSINGHOFF

Commissioner of Patents and Trademarks